(12) United States Patent
Zima et al.

(10) Patent No.: US 7,491,412 B2
(45) Date of Patent: Feb. 17, 2009

(54) PROCESS FOR THE RECOVERY OF A PHYTOLIPID COMPOSITION

(75) Inventors: George Chester Zima, Kingsport, TN (US); Terry Ann Oldfield, Kingsport, TN (US); Suzanne Winegar Dobbs, Kingsport, TN (US); Phillip Michael Cook, Kingsport, TN (US); Charles Everette Kelly, Kingsport, TN (US); Mary Caraway Crow, Kingsport, TN (US); Craig Alan Hoyme, Kingsport, TN (US)

(73) Assignee: Eastman Chemical Company, Kingsport, TN (US)

( * ) Notice: Subject to any disclaimer, the term of this patent is extended or adjusted under 35 U.S.C. 154(b) by 770 days.

(21) Appl. No.: 10/844,074

(22) Filed: May 12, 2004

(65) Prior Publication Data

US 2005/0053712 A1    Mar. 10, 2005

Related U.S. Application Data

(63) Continuation-in-part of application No. 10/659,620, filed on Sep. 10, 2003, now Pat. No. 7,416,756.

(51) Int. Cl.
  *A01N 65/00* (2006.01)
  *A01N 43/16* (2006.01)
(52) U.S. Cl. .................................. 424/725; 514/458
(58) Field of Classification Search ................. None
  See application file for complete search history.

(56) References Cited

U.S. PATENT DOCUMENTS

| | | | |
|---|---|---|---|
| 4,218,334 A | 8/1980 | Lundmark | |
| 4,454,159 A | 6/1984 | Musher | |
| 4,550,183 A | 10/1985 | Willging | |
| 4,603,142 A | 7/1986 | Burger et al. | |
| 4,844,890 A | 7/1989 | Suskin | |
| 5,215,759 A | 6/1993 | Mausner | |
| 5,346,697 A | 9/1994 | Tokuyama et al. | |

(Continued)

FOREIGN PATENT DOCUMENTS

DE    3615029    5/1986

(Continued)

OTHER PUBLICATIONS

Itoh, T. 1973. Sterol Composition of 19 Vegetable Oils. JAOAC 50(4)122-125.*

(Continued)

*Primary Examiner*—Patricia Leith
*Assistant Examiner*—Qiuwen Mi
(74) *Attorney, Agent, or Firm*—Brett L. Nelson; Bernard J. Graves, Jr.

(57) ABSTRACT

Disclosed is a process for the recovery of a phytolipid composition from a vegetable oil by-product. The phytolipid composition produced comprises squalene, phytosterols, mixed tocopherols and tocotrieneols, and vegetable wax and is useful as an emollient. The phytochemical composition may be applied directly to the skin to provide emolliency. Alternatively, the phytolipid composition may be formulated in various aqueous or anhydrous cosmetic compositions such as creams, lotions, gels, ointments, lip balms, sticks, or pencils for treatment of the skin and lips. The phytolipid composition also may be incorporated into foods, beverages, and nutraceuticals to provide health benefits.

6 Claims, 1 Drawing Sheet

U.S. PATENT DOCUMENTS

| | | | |
|---|---|---|---|
| 5,362,418 A | 11/1994 | Yamasaki et al. | |
| 5,378,461 A | 1/1995 | Neigut | |
| 5,444,096 A | 8/1995 | McCrea et al. | |
| 5,466,457 A * | 11/1995 | Schneider et al. | 424/401 |
| 5,487,817 A * | 1/1996 | Fizet | 203/38 |
| 5,494,657 A | 2/1996 | Swenson | |
| 5,496,861 A | 3/1996 | Rouse, III et al. | |
| 5,558,871 A | 9/1996 | Griat et al. | |
| 5,589,515 A | 12/1996 | Suzuki et al. | |
| 5,631,248 A | 5/1997 | Davis et al. | |
| 5,650,139 A | 7/1997 | Nojima | |
| 5,653,966 A | 8/1997 | Bertoli et al. | |
| 5,660,691 A | 8/1997 | Barnicki et al. | |
| 5,662,912 A | 9/1997 | Moeller et al. | |
| 5,667,791 A | 9/1997 | Hersh et al. | |
| 5,679,374 A | 10/1997 | Fanchon et al. | |
| 5,681,551 A | 10/1997 | Nojima | |
| 5,688,752 A | 11/1997 | Turner | |
| 5,700,396 A | 12/1997 | Suzuki et al. | |
| 5,733,572 A | 3/1998 | Unger et al. | |
| 5,744,145 A | 4/1998 | Bertoli et al. | |
| 5,747,049 A | 5/1998 | Tominaga | |
| 5,776,441 A | 7/1998 | Scancarella et al. | |
| 5,811,111 A | 9/1998 | McAtee et al. | |
| 5,843,499 A * | 12/1998 | Moreau et al. | 426/2 |
| 5,853,705 A | 12/1998 | Nakayama et al. | |
| 5,871,759 A | 2/1999 | Hamano et al. | |
| 5,882,660 A | 3/1999 | Chambers et al. | |
| 5,945,409 A | 8/1999 | Crandall | |
| 5,952,393 A | 9/1999 | Sorkin, Jr. | |
| 5,993,850 A | 11/1999 | Sankaram et al. | |
| 6,008,246 A | 12/1999 | Ito et al. | |
| 6,022,577 A | 2/2000 | Chrysam et al. | |
| 6,025,348 A | 2/2000 | Goto et al. | |
| 6,045,779 A | 4/2000 | Mueller et al. | |
| 6,066,316 A | 5/2000 | Shiojima et al. | |
| 6,077,520 A | 6/2000 | Tominaga | |
| 6,087,353 A | 7/2000 | Stewart et al. | |
| 6,117,419 A | 9/2000 | Vernice | |
| 6,139,897 A | 10/2000 | Goto et al. | |
| 6,153,209 A | 11/2000 | Vega et al. | |
| 6,190,680 B1 | 2/2001 | Sakurada et al. | |
| 6,193,986 B1 | 2/2001 | Sakurada | |
| 6,197,832 B1 | 3/2001 | Sorkin, Jr. | |
| 6,204,290 B1 | 3/2001 | Lane et al. | |
| 6,210,693 B1 | 4/2001 | Inoue et al. | |
| 6,224,717 B1 | 5/2001 | Sumner, Jr. et al. | |
| 6,277,431 B1 | 8/2001 | Berry et al. | |
| 6,284,257 B1 | 9/2001 | Khayat et al. | |
| 6,284,802 B1 | 9/2001 | Bissett et al. | |
| 6,306,898 B1 | 10/2001 | Shimizu et al. | |
| 6,309,653 B1 | 10/2001 | Hamano et al. | |
| 6,316,428 B1 | 11/2001 | Crandall | |
| 6,326,050 B1 | 12/2001 | Goto et al. | |
| 6,361,782 B1 | 3/2002 | Chevalier et al. | |
| 6,365,656 B1 | 4/2002 | Green et al. | |
| 6,410,762 B1 | 6/2002 | Rao et al. | |
| 6,458,379 B1 | 10/2002 | Konno et al. | |
| 6,485,756 B1 | 11/2002 | Aust et al. | |
| 6,488,941 B1 * | 12/2002 | Burnier et al. | 424/401 |
| 6,491,902 B2 | 12/2002 | Shefer et al. | |
| 6,514,505 B2 | 2/2003 | Dorf | |
| 6,534,047 B1 | 3/2003 | Bodelin | |
| 6,534,074 B2 | 3/2003 | Krzysik et al. | |
| 6,552,208 B1 | 4/2003 | Alander et al. | |
| 6,582,748 B1 | 6/2003 | Loh et al. | |
| 6,589,538 B1 | 7/2003 | Lemann et al. | |
| 6,635,262 B2 | 10/2003 | Jourdan et al. | |
| 6,677,469 B1 | 1/2004 | Dunford et al. | |
| 6,716,451 B1 | 4/2004 | Udell et al. | |
| 6,828,451 B2 | 12/2004 | Barrault et al. | |
| 6,846,941 B2 | 1/2005 | Rohr et al. | |
| 6,896,911 B2 | 5/2005 | Indira et al. | |
| 6,911,211 B2 | 6/2005 | Eini et al. | |
| 6,946,123 B2 | 9/2005 | De La Poterie et al. | |
| 6,949,262 B1 | 9/2005 | Smothers | |
| 6,967,023 B1 | 11/2005 | Eini et al. | |
| 6,979,440 B2 | 12/2005 | Shefer et al. | |
| 6,991,813 B2 | 1/2006 | Xu | |
| 6,994,863 B2 | 2/2006 | Eini et al. | |
| RE39,043 E | 3/2006 | Nakayama et al. | |
| 7,090,860 B2 | 8/2006 | Yousi et al. | |
| 7,157,110 B2 | 1/2007 | Loh et al. | |
| 7,157,413 B2 | 1/2007 | Lazzeri et al. | |
| 7,166,300 B1 * | 1/2007 | Dascalu | 424/464 |
| 2002/0012640 A1 | 1/2002 | Mohammadi et al. | |
| 2002/0022009 A1 | 2/2002 | De La Poterie | |
| 2002/0025303 A1 | 2/2002 | Fructus et al. | |
| 2002/0085982 A1 | 7/2002 | Dorf | |
| 2002/0098217 A1 | 7/2002 | Piot et al. | |
| 2002/0107292 A1 | 8/2002 | Bortlik et al. | |
| 2002/0142083 A1 | 10/2002 | Jacobs | |
| 2002/0155962 A1 | 10/2002 | Cincotta et al. | |
| 2002/0192251 A1 | 12/2002 | Collin | |
| 2003/0026856 A1 | 2/2003 | Aust et al. | |
| 2003/0053974 A1 | 3/2003 | Shefer et al. | |
| 2003/0086897 A1 | 5/2003 | Ohta et al. | |
| 2003/0086949 A1 | 5/2003 | Perrier et al. | |
| 2003/0086951 A9 | 5/2003 | Piot et al. | |
| 2003/0096876 A1 | 5/2003 | Gamble et al. | |
| 2003/0108579 A1 | 6/2003 | Yousfi et al. | |
| 2003/0120095 A1 | 6/2003 | Rohr et al. | |
| 2003/0130532 A1 | 7/2003 | Bardet et al. | |
| 2003/0157138 A1 | 8/2003 | Eini et al. | |
| 2003/0176540 A1 | 9/2003 | Rajasekharan et al. | |
| 2003/0186818 A1 | 10/2003 | Reaney | |
| 2003/0190335 A1 | 10/2003 | Boussouira et al. | |
| 2003/0195367 A1 | 10/2003 | Barrault et al. | |
| 2003/0206934 A1 | 11/2003 | Riedel et al. | |
| 2004/0001793 A1 | 1/2004 | Dorf | |
| 2004/0009201 A1 | 1/2004 | Collin et al. | |
| 2004/0018250 A1 | 1/2004 | Ceccoli et al. | |
| 2004/0022752 A1 | 2/2004 | De La Poterie | |
| 2004/0023894 A1 | 2/2004 | Hasler-Nguyen et al. | |
| 2004/0043045 A1 | 3/2004 | Seipel et al. | |
| 2004/0052921 A1 | 3/2004 | Loh et al. | |
| 2004/0126401 A1 | 7/2004 | Collin | |
| 2004/0142007 A1 | 7/2004 | Moussou et al. | |
| 2004/0161435 A1 | 8/2004 | Gupta | |
| 2004/0192948 A1 | 9/2004 | Indira et al. | |
| 2004/0223986 A9 | 11/2004 | Boussouira et al. | |
| 2004/0253275 A1 | 12/2004 | Eini et al. | |
| 2004/0253276 A1 | 12/2004 | Sato et al. | |
| 2005/0051419 A1 | 3/2005 | Zima et al. | |
| 2005/0250953 A1 * | 11/2005 | May et al. | 549/413 |
| 2006/0099231 A1 | 5/2006 | De La Poterie et al. | |
| 2006/0134038 A1 | 6/2006 | De La Poterie et al. | |

FOREIGN PATENT DOCUMENTS

| | | |
|---|---|---|
| DE | 196 52 522 | 6/1998 |
| EP | 467218 | 1/1992 |
| EP | 0 919 225 | 6/1999 |
| EP | 1097985 | 5/2001 |
| EP | 1 108 364 | 6/2001 |
| JP | 03127730 A | 5/1991 |
| JP | 09169638 | 6/1997 |
| JP | 163764 | 6/2001 |
| WO | WO 0151596 | 7/2001 |
| WO | WO 02/26207 | 4/2002 |

OTHER PUBLICATIONS

Lee, Frank A. 1975. Basic Food Chemistry. AVI Publishing Company, Inc., Westport, CT. p. 95-96.*

Grant, J. 1969. Hackh;s Chemical Dictionary, 4th edition, McGraw-Hill Book Company, New York, p. 721-722.*

Rose, A. and Rose, E. 1966. The Condensed Chemical Dictionary. Reinhold Publishing Corporation. p. 887 & 1016.*

Office Action date of mailing Aug. 18, 2006 received on co-pending U.S. Appl. No. 10/659,620.

Office Action date of mailing May 31, 2007 received on co-pending U.S. Appl. No. 10/659,620.

Itoh, T. 1973. Sterol Composition of 19 Vegetable Oils. JAOAC 50(4) 122-125.

Grant, J. 1969. Hackh's Chemical Dictionary, 4th Edition, McGraw-Hill Book Comapny, New York, p. 721-722.

Office Action dated Aug. 10, 2007 received on co-pending Chinese Application for Invention No. 200480025752.8.

De Paepe, Kristien, Cosmetic Lipids and the Skin Barrier, Foerster, Thomas, Ed. Marcel Dekker; New York, 2002; pp. 149-153.

Lanzendorfer, Ghita, Cosmetic Lipids and the Skin Barrier, Foerster, Thomas, Ed. Marcel Dekker, New York, 2002; pp, 271-290.

Chang, Chiehming J. et al., Chromatographic Isolation for Non-Glyceride Components; Supercritical Carbon Dioxide Extraction of High-Value Substances from Soybean Oil Deodorizer Distillate, Industrial and Engineering Chemistry Research (2000), 39 (12), pp. 4521-4525.

Binder, Thomas P., ADM Research Processing Deodorizer Distillate for Value-Added Products, Abstracts of Papers, 225th ACS National Meeting, New Orleans, LA Mar. 23-27, 2003, AGFD-AA3, American Chemical Society.

A. A. Qureshi et al., Dietary Tocotrienols Reduce Concentrations of Plasma Cholesterol, Apolipoprotein B., Thromboxane B. sub. 2 and Platelet Factor 4 in Pigs with Inherited Hyperlipidemias, Am. J. Clin, Nutr., pp. 1042S-1046S (1991).

A. A. Qureshi et al., Lowering of Serum Cholesterol In Hypercholesterolemic Human By Tocotrienols (Palmivitee), Am. J. Clin, Nutr., 53, pp. 1021S-1026S (1991).

D.T.S. Tan et al., The Effect of Palm Oil Vitamin E Concentrate On the Serum and Lipoprotein Lipids in Humans, Am. J. Clin. Nutr., 53, pp. 1027S-1030S (1991).

E. Niki et al., Inhibition of Oxidation of Biomembranes By Tocopherol, Annals of the New York Academy of Sciences, 570, pp. 23-31 (1989).

K. Fukuzawa et al., Increased Platelet-Activating Factor (PAF) Synthesis in Polymorphonuclear Leukocytes of Vitamin E-Deficient Rats, Annals of the New York Academy of Sciences, 570, pp. 449-454 (1989).

W. A. Skinner et al., Antioxidant Properties of alpha-Tocopherol Derivatives and Relationships of Antioxidant Activity to Biological Activity, Lipids, 5(2), pp. 184-186 (1969).

A. T. Diplock, Relatioship of Tocopherol Structure to Biological Activity, Tissue Uptake, and Prostaglandin Biosynthesis, Annals of the New York Academy of Sciences, 570, pp. 72-84 (1989).

Moller, Hinrich, Cosmetics Lipids and the Skin Barrier, p. 5 Foerster, Thomas, Ed. Marcel Dekker; New York, 2002, p. 5.

* cited by examiner

PROCESS FOR THE RECOVERY OF A PHYTOLIPID COMPOSITION

CROSS REFERENCE TO RELATED APPLICATION

This application is a continuation-in-part of application Ser. No. 10/659,620 filed Sep. 10, 2003, now U.S. Pat No. 7,416,756.

FIELD OF THE INVENTION

This invention pertains to a process for the recovery of a phytolipid composition from a vegetable oil by-product. The composition comprises squalene, phytosterols, mixed tocopherols and tocotrieneols (mixed tocols), and vegetable wax and is useful as an emollient. The phytolipid composition may be applied directly to the skin to provide emolliency. Alternatively, the composition may be formulated in various aqueous or anhydrous cosmetic compositions such as creams, lotions, gels, ointments, balms, sticks, or pencils for treatment of the skin including the lips. The phytolipid composition can also be incorporated into foods, beverages, and nutraceuticals to provide health benefits.

BACKGROUND OF THE INVENTION

U.S. Pat. No. 5,660,691 describes a process for the production of tocotrienol/tocopherol blend concentrates from vegetable oil by-products such as deodorizer distillates, steam refining distillates, acidulated soapstock and other vegetable oil by-products rich in tocotrienol. U.S. Pat. No. 6,224,717 discloses solvent/water mixtures in connection with the separation of tocotrienol from tocol-containing mixtures. According to U.S. Pat. No. 6,224,717, DE 3615029 discloses the purification of tocopherols by contacting a tocopherol containing substance with neat methanol to form two layers, separating the methanol layer, cooling the methanol layer to produce a methanol phase and a raffinate layer, and recovering the tocopherols from the methanol layer. A disadvantage of this method is that a considerable amount of tocopherols are lost to the raffinate, thereby reducing the overall recoverable yield. U.S. Pat. No. 4,550,183 discloses extracting a tocopherol containing material with caustic methanol to produce a two-phase system. The methanol layer is removed and neutralized with acid. A disadvantage of this method is that an additional step is required to neutralize the basic methanol layer. JP 03127730 A discloses extracting an unsaturated oil or fat with a neat extraction solvent composed of neat butanol, ethylene glycol, methyl ethyl ketone, acetone, benzene, or cyclohexane followed by a series of distillation steps.

Published U.S. Patent Application 20020142083 entitled Process for the Production of Tocotrienols uses "solvent wintering" as a process step in the preparation of tocotrienols. Wintering is the cooling of oil, with or without added solvent, to effect the crystallization of sterols and sterol like materials.

Disclosures pertaining to processes for separating or recovering components of vegetable oil sources include U.S. Pat. No. 6,552,208; WO 200151596, Isolation of Non-Saponifiables from Vegetable Oils; EP 1097985 (Chemical Abstracts 2325224), Chromatographic Isolation for Non-Glyceride Components; Chang, Chiehming J. et al., *Supercritical Carbon Dioxide Extraction of High-Value Substances from Soybean Oil Deodorizer Distillate*, Industrial & Engineering Chemistry Research (2000), 39 (12), 4521-4525; Binder, Thomas P., ADM Research, *Processing Deodorizer Distillate for Value-Added Products*, Abstracts of Papers, 225th ACS National Meeting, New Orleans, La. Mar. 23-27, 2003, AGFD-113, American Chemical Society.

The outer-most layer of human skin, the stratum corneum, provides the barrier function of the skin, preventing dehydration of underlying tissues and preventing absorption of various undesirable substances into the body. The stratum corneum consists of dead cells that are surrounded by proteins and lipids. It is primarily the lipid layer that provides the barrier function of the skin. Both squalene and sterols (predominately cholesterol) are natural components of the stratum corneum lipid layer. See, for example, De Paepe, Kristien, *Cosmetic Lipids and the Skin Barrier*; Foerster, Thomas, Ed. Marcel Dekker: New York, 2002; pages 152-153). Squalene is a major component of sebum secreted by the sebaceous glands (Moller, Hinrich, *Cosmetic Lipids and the Skin Barrier*, p 5). The benefits of lipids in cosmetics are discussed in detail by Lanzendorfer, Ghita in Cosmetic *Lipids and the Skin Barrier*, pages 271-290).

Several patents cite the use of the various components of lipid compositions, individually and in combinations with one another, to provide benefits to the skin, including the lips, or to the personal care product itself. U.S. Pat. No. 6,306,898 (WO 9632933) describes four aspects of preparations for treating dermatoses. The third aspect comprises a nonsteroidal anti-inflammatory agent, vitamin E, and squalane and/or squalene. The fourth aspect comprises an antihistaminic agent, vitamin E, and squalane and/or squalene. The vitamin E in combination with squalane or squalene is described as having a synergistic therapeutic effect in cooperation with the nonsteroidal anti-inflammatory agent or antihistaminic agent, respectively.

U.S. Pat. No. 5,494,657 describes the use of compositions comprising petrolatum, squalene or hydrogenated polybutene, non-hydrogenated polybutene, a fatty acid or fatty acid ester, and an antioxidant for moisturizing skin. The antioxidant is described as comprising a natural or synthetic alpha-tocopherol. One object of U.S. Pat. No. 5,494,657 is to provide skin care compositions similar to natural sebum. This patent teaches that the combination of polybutenes, the fatty acid or fatty acid ester, and anti-oxidant provides a balanced formulation that protects the skin while allowing controlled oxygen permeability. U.S. Pat. No. 5,378,461 describes a composition for topical treatment of damaged skin comprising a carrier solution consisting of squalene or squalane, a ubiquinone (coenzyme Q), and vitamins E, A, and D. Squalane and squalene have each been shown to be a very effective transport medium for the other ingredients. U.S. Pat. No. 5,378,461 teaches that squalene is a natural emollient since it is synthesized in the sebaceous glands and Vitamin E is known to serve as an antioxidant—reducing or eliminating lipid peroxidation.

U.S. Pat. No. 4,454,159 describes preparations for the treatment of irritated, pruritic, and dry skin conditions that contain glycerol trioleate, a glyceride oil, hydrogenated glyceride oil, lecithin, tocopherol, a humectant, isopropyl palmitate, squalene or squalane, and a collagen product. The lipids used in the preparations should be rich in tocopherol. The compositions of U.S. Pat. No. 4,454,159 were found to exhibit unusual skin therapy in their ability to relieve skin irritation and itching. WO 2002026207 describes a cosmetic formulation that is characterized by a lipid composition comprising squalene which approximates human sebum. The compositions also contain natural vitamin E acetate. JP 09169638 describes a composition for treating dermatological diseases containing astringent (0.9-50%), vitamin E (0.1-99%), and squalane and/or squalene (0.1-99%). The astringent is preferably tannic acid, zinc oxide, or potassium aluminum sulphate. Patents that mention both squalene and vitamin E (or tocopherol) as ingredients in skin care formulations, refer to them as optional ingredients or include them in long lists of optional components. The art does not attribute any particular benefit to the combination of squalene and tocopherol in skin care formulations.

The following publications pertain to the use of sterols or phytosterols in skin care applications. U.S. Pat. No. 6,534,074 describes a composition applied to "a body facing material" that enhances skin barrier properties. The composition comprises natural fats or oils, sterols or sterol derivatives, a surfactant, a humectant, an emollient, a wax, and an oil soluble or dispersible viscosity enhancer. The specific benefit of including sterols or sterol derivatives in the formulation is not discussed. Rice bran wax is not included in the list of waxes that can be used as the wax component.

U.S. Pat. No. 6,284,802 describes a method for regulating the condition of mammalian keratinous tissue by applying a composition comprising farnesol, other skin care actives, and a carrier. Antioxidant and anti-inflammatory agents are listed as possible skin care actives. The antioxidant is selected from a group that includes tocopherol; and the anti-inflammatory agent is selected from a group that includes phytosterol. U.S. Pat. No. 6,153,209 describes an article for applying a skin care composition to the skin. The skin care composition is further described as comprising an emollient, a permeability agent, and an immobilizing agent. Sterols and sterol esters are included in the list of possible emollients; squalene is included in the list of possible permeability agents; and wax is included in the list of immobilizing agents. Rice bran wax is not included in the list of waxes that are specifically mentioned as possible waxes. The skin care composition can further comprise an antioxidant selected from a group that includes tocopherols and mixed tocopherols.

U.S. Pat. No. 5,882,660 describes a personal care composition in the form of an aqueous liquid comprising a lipid composition, a surface-active agent, and a cationic polymer. The lipid composition comprises two components, one of which is selected from a group that includes 3-beta-sterol and squalene. Examples of 3-beta-sterols include cholesterol, sitosterol, stigmasterol and ergosterol. This patent discloses that cholesterol is a vital component of the natural skin lipids that constitute the moisture barrier in the stratum corneum. U.S. Pat. No. 5,733,572 (WO 9109629) describes a gas filled lipid-containing microsphere comprising a therapeutic agent or cosmetic for topical application. Among the many components that can make up the composition are vitamins, including vitamin E; ointment bases including squalene; and a biocompatible lipid, including cholesterols, tocopherols, and non-ionic lipids.

U.S. Pat. No. 5,688,752 describes an aqueous liquid personal care cleansing composition comprising three components. One of the components is selected from a group that includes 3-beta-sterol and squalene. EP 467218 describes a lipid composition for cosmetics comprising fatty acids and/or their tocopheryl esters (0-95%), n-alkanes (0-65%), squalene (0-30%), cholesterol and/or lanolin alcohol (0-50%), triglycerides (0-80%), and/or wax esters (0-60%), where at least 2 of these components must be present. Also described is a skin oil containing the above lipid composition (10%).

Both U.S. Pat. Nos. 4,218,334 and 6,087,353 discuss the problem of solubilizing or dispersing phytosterols in emulsions and other formulations. U.S. Pat. No. 4,218,334 proposes that this problem may be solved by making a blend of phytosterol with free fatty acids or saturated free fatty alcohols. U.S. Pat. No. 6,087,353 proposes a solution to the problem that includes esterifying, then hydrogenating, the phytosterol. U.S. Pat. No. 6,087,353 also discusses the need to enhance the stability of phytosterol compositions.

The following publications pertain to the use of lipid compositions in food, nutritional, and pharmaceutical applications. U.S. Pat. Nos. 5,952,393 and 6,197,832 describe compositions and method for reducing serum cholesterol in humans and animals. The method comprises administering phytosterol and policosanol which together produce a synergistic effect in lowering serum cholesterol levels. Preferably, the administered composition includes about 3.2:1 parts by weight of phytosterol and policosanol. U.S. Pat. Nos. 6,025,348, 6,139,897 and 6,326,050 describe oil or fat compositions comprising 15 or more weight percent of a diacylglycerol and 1.2 to 20 weight percent phytosterol dissolved or dispersed in the fat and oil. U.S. Pat. No. 6,087,353 provides an esterified and subsequently hydrogenated phytosterol composition for use alone or for incorporation into foods, beverages, pharmaceuticals, nutraceuticals, and the like. The composition has the advantage of enhanced solubility/dispersibility, increased molar potency and enhanced stability over naturally isolated phytosterol compositions. Methods for the esterification and subsequent hydrogenation of the phytosterols are also provided.

U.S. Pat. No. 6,204,290 pertains to novel tocotrienols and tocotrienol-like compounds that exhibit biological activity. This patent discloses that the tocotrienols and tocotrienol-like compounds may be conveniently obtained from biological sources or by chemical synthesis and may be used in pharmaceutical compositions, foodstuffs and dietary supplements. U.S. Pat. No. 6,204,290 also discloses the use of tocotrienols, tocotrienol-like compounds, and mixtures thereof, as hypocholesterolemic, antithrom-botic, antioxidizing, antiatherogenic, antiinflammatory and immunoregulatory agents, or as agents useful to decrease lipoprotein (a) concentration in the blood or to increase feed conversion efficiency.

U.S. Pat. No. 6,277,431 describes an edible oil that decreases the synthesis, absorption and blood level of cholesterol by a human patient, increases the excretion of cholesterol from the human patient, curtails accumulation of peroxidized material in the blood of the human patient, and also increases the blood level of vitamin E in said human patient. The edible oil is comprised of about 10 to 30% tocopherols, tocotrienols or combinations thereof; about 2 to 20% free sterols; about 2 to 20% sterol esters; about 0.1 to 1.0% of cycloartenols; and; about 7 to 19% of saturated fats, wherein all percentages are weight/weight.

Sterols are naturally occurring triterpenoids that perform many critical cellular functions, and so phytosterols have received a great deal of attention due to their ability to decrease serum cholesterol levels when fed to a number of mammalian species, including humans. Phytosterols such as campesterol, stigmasterol and beta-sitosterol in plants, ergosterol in fungi and cholesterol in animals are each primary components of cellular and sub-cellular membranes in their respective cell types. The dietary source of phytosterols in humans comes from plant materials, i.e., vegetables and plant oils. The estimated daily phytosterol content in the conventional western-type diet is approximately 60-80 milligrams in contrast to a vegetarian diet that provides about 500 milligrams per day.

Plant constituents have been proven useful in the prevention and treatment of a wide variety of diseases and conditions. Recent studies have indicated that tocotrienols may be biologically active. For example, U.S. Pat. No. 4,603,142 identifies d-alpha-tocotrienol, isolated from barley extracts, as an inhibitor of cholesterol biosynthesis. See also A. A.

Qureshi et al. (1986), supra. Various human and animal studies have confirmed the impact of pure tocotrienols, isolated from barley, oats and palm oil, on cholesterol biosynthesis, specifically LDL-cholesterol (A. A. Qureshi et al., *Dietary Tocotrienols Reduce Concentrations of Plasma Cholesterol, Apolipoprotein B, Thromboxane B. sub.2 and Platelet Factor 4 In Pigs With Inherited Hyperlipidemias*, Am. J. Clin. Nutr., pp. 1042S-46S (1991); A. A. Qureshi et al., *Lowering Of Serum Cholesterol In Hypercholesterolemic Humans By Tocotrienols (Palmvitee)*, Am. J. Clin. Nutr., 53, pp. 1021 S-26S (1991); D. T. S. Tan et al., *The Effect Of Palm Oil Vitamin E Concentrate On The Serum And Lipoprotein Lipids In Humans*, Am. J. Clin. Nutr., 53, pp. 1027S-30S (1991)).

Other chromanols, the tocopherols, including d-α-tocopherol (vitamin E), have been extensively studied. As a result of these studies, certain biological activities have been attributed to the tocopherols. Such activities include platelet aggregation and antioxidant functions. See, for example, E. Niki et al., *Inhibition of Oxidation of Biomembranes By Tocopherol*, Annals of the New York Academy of Sciences, 570, pages 23-31 (1989) and K. Fukuzawa et al., *Increased Platelet-Activating Factor (PAF) Synthesis in Polymorphonuclear Leukocytes of Vitamin E-Deficient Rats*, Annals of the New York Academy of Sciences, 570, pages 449-453 (1989)). Although the exact structure-function relationship is not known, several experiments have highlighted the importance of the phytyl side chain in the biological activity of tocopherols. See W. A. Skinner et al., *Antioxidant Properties of .alpha.-Tocopherol Derivatives and Relationships of Antioxidant Activity to Biological Activity*, Lipids, 5(2), pp. 184-186 (1969) and A. T. Diplock, *Relationship of Tocopherol Structure to Biological Activity, Tissue Uptake, and Prostaglandin Biosynthesis*, Annals of the New York Academy of Sciences, 570, pp. 73-84 (1989)).

BRIEF SUMMARY OF THE INVENTION

The process provided by the present invention recovers a phytolipid composition comprising squalene, phytosterols, mixed tocols and vegetable wax from a vegetable oil by-product. An embodiment of the invention pertains to a process for preparing a lipid composition comprising squalene, phytosterols, tocopherols and vegetable wax which comprises the steps of:

(1) distilling a vegetable oil by-product comprised of mixed tocols, fatty acids, hydrocarbons, vegetable waxes, sterol esters of fatty acids, sterols, triterpenoid alcohols, squalene, methyl-sterols, and mono-, di-, and triglycerides at a temperature of about 170 to about 320° C., preferably about 240 to about 290° C., and a pressure of about 0.05 to about 35 torr, preferably about 0.2 to about 20 torr, to produce (i) a vapor product comprising fatty acids and low boiling hydrocarbons and (ii) a liquid product, i.e., the distillation residue or bottoms;

(2) distilling the liquid product of step (1) at a temperature of about 230 to about 300° C., preferably about 240 to about 260° C., and a pressure of about 0.0005 to about 1 torr, preferably about 0.005 to about 0.5 torr, to produce (i) a second vapor product comprising a mixed tocols concentrate, squalene, phytosterols, and vegetable wax and (ii) a second liquid product, i.e., a second distillation residue or bottoms;

(3) intimately contacting the condensed vapor product from step (2) with an extractant selected from alkanols and mixtures of acetone and water followed by separation of the resulting mixture into two phases comprising (i) a first phase comprising a majority of the extractant and (ii) a second phase comprising a majority of the condensed vapor effluent from step (2)

(4) collecting the second phase formed in step (3);

(5) cooling the first phase formed in step (3) to effect formation of a precipitate followed by collection of the precipitate; and (6) combining the second phase collected in step (4) with the precipitate collected in step (5) and removing the extractant employed in step (3) from the materials collected in steps (4) and (5);

whereby a phytolipid composition comprising about 10 to about 40 weight percent squalene, about 2 to about 20 weight percent phytosterols, about 1 to about 10 weight percent of mixed tocols and about 40 to about 80 weight percent vegetable wax is obtained.

A second embodiment of the invention is a phytolipid composition consisting essentially of about 10 to about 40 weight percent squalene, about 2 to about 20 weight percent phytosterols, about 1 to about 10 weight percent of mixed tocols and about 40 to about 80 weight percent vegetable wax. Another embodiment of the present invention is a skin care preparation intended for application to human skin comprising the above-described phytolipid composition. Yet another embodiment of the invention is an admixture of the above-described phytolipid composition and water such as an emulsion. The skin care preparations and admixtures provided by the present invention may contain various additional ingredients typically present in skin care compositions. The skin care preparations and admixtures also may be used as a vehicle for the delivery of various dermatologically-active pharmaceutical ingredients to human skin.

Another embodiment of our invention is a food product comprising the above-described phytolipid composition. The food product may be a table spread such as margarine or mayonnaise, baked goods or beverages including both non-alcoholic and alcoholic beverages. Finally, the phytolipid compositions may be incorporated into dietary supplements and therapeutic preparations for oral consumption to provide a combination of phytosterols and tocols that have been found to provide the benefits discussed herein above. Such supplements and preparations may be in the form of unit dosages comprising an oil and the phytolipid composition, e.g., about 1 to about 10,000 ppm phytolipid composition in mineral oil or an edible oil.

BRIEF DESCRIPTION OF THE DRAWING

The accompanying

DETAILED DESCRIPTION

Figure 1:
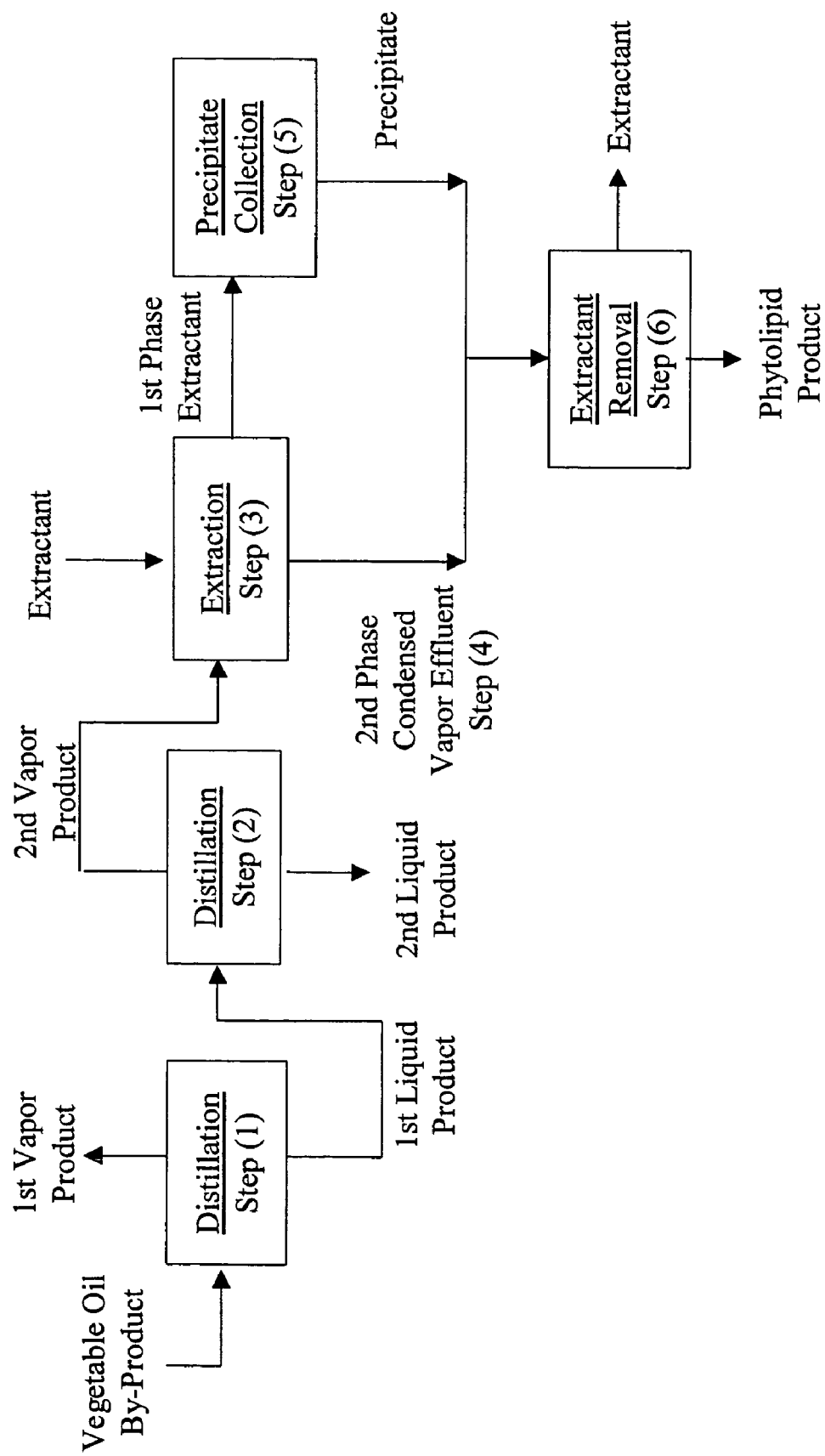
FIG. 1 is a process flow diagram illustrating a system embodying the principles of the present invention. While the invention is susceptible to embodiment in various forms, there is shown in the accompanying FIG. 1 and hereinafter described in detail a preferred embodiment of the invention. The present disclosure is to be considered as an exemplification of the invention without limitation to the specific embodiment illustrated.

The vegetable oil by-product utilized in the process of the present invention may be a deodorizer distillate, steam refining distillate, acidulated soapstock or other by-product material typically produced in the processing of vegetable oils. The vegetable oil by-product preferably is derived from palm oil, soybean oil, corn oil or, most preferably, from rice bran oil. The vegetable oil by-product comprises free fatty acids, mixed tocols, hydrocarbons, sterols, sterol esters of fatty acids, squalene, triterpenoid alcohols, methylsterols, mono-, di- and tri-glycerides, and vegetable wax, e.g., a mixture of dehydrated sterols, linear hydrocarbons such as nonacosane ($C_{29}H_{60}$), and other hydrocarbons. In the first step of the process, the vegetable oil by-product is distilled under high vacuum to remove free fatty acids and other low boilers. The first distillation typically removes about 50 to about 90 weight percent, preferably about 60 to about 80 weight percent, of the free fatty acids present. The first distillation is carried out at a temperature of about 170 to about 320° C., preferably about 240 to about 290° C., and a pressure of about 0.1 to about 35 torr, preferably about 0.2 to about 20 torr. The first distillation normally is carried out in a high-vacuum apparatus that involves thin film evaporation such as a short-path evaporator, a thin-film evaporator, a centrifugal molecular still, a falling film evaporator or any combination of such apparatus capable of low pressure operation. A short-path evaporator is a wiped surface evaporator that utilizes an internal condenser to achieve low pressures. A thin-film evaporator is a wiped surface evaporator that utilizes an external condenser. The evaporation surfaces of these devices are heated using an external circulated hot oil bath. Vacuum is provided by a staged vacuum system comprised of liquid ring vacuum pumps or blowers, and a booster diffusion pump. The vapor product from the first distillation typically is at least 10 weight percent, more typically from about 20 to about 40 weight percent, of the vegetable oil by-product distilled.

In the second step of the process, the liquid residue or product from step (1) is distilled at a temperature of about 230 to about 300° C., preferably about 240 to about 260° C., and a pressure of about 0.0005 to about 1 torr, preferably about 0.005 to about 0.5 torr, to produce a vapor product comprising a tocotrienol/tocopherol concentrate, squalene, phytosterols, and vegetable wax. The vapor product from the second distillation typically is at least 15 weight percent, more typically from about 20 to about 50 weight percent, of the starting material employed in the second distillation, i.e., the liquid residue or product from step (1). The liquid residue or product resulting from the second distillation comprises triglycerides, sterol esters, other high-boiling fatty acid esters and other high-boiling components.

The process of the present invention does not include a separate esterification step wherein the vegetable oil by-product is heated, optionally in the presence of an esterification catalyst, to cause esterification of free sterols with fatty acids present in the vegetable oil by-product or added fatty acids. Such an esterification step may be carried out prior to distillation while water is removed from the esterification mixture, but doing so will reduce the content of sterols present by converting the sterols to sterol esters.

In the third step of the process, the condensed vapor effluent from step (2) is intimately contacted, e.g., by agitation, with an extractant (or extraction agent) that is immiscible with the condensed vapor effluent from step (2). The extractant may be selected from alkanols and mixtures of acetone and water. The density of the extractant is less than the density of the blend concentrate, preferably less than 1. Examples of the alkanol extractants that may be used include methanol, ethanol, propanol, 2-propanol, butanol, isobutanol, cychexanol, 2-ethylhexanol, and the like. The acetone-water mixtures preferably consist of acetone:water weight ratios of about 74:26 to about 80:20. Methanol, ethanol, propanol and 2-propanol represent the preferred extractants with methanol being particularly preferred. The amount of extractant employed is, in general, not critical provided that the amount of extractant will result in the formation of a two-phase mixture, e.g., the amount of extractant should be greater than the amount that is soluble in the condensed vapor effluent from step (2). The volume:volume ratio of extract:condensed vapor effluent from step (2) typically will be about 0.5:1 to about 25:1 and preferably is about 6:1 to about 12:1.

The means for achieving the agitation or intimate contacting are well-known in the art. Extraction techniques include single contact extraction, i.e., batch operation, simple multi-stage contact extraction, countercurrent multistage extraction, true continuous countercurrent extraction, and continuous countercurrent extraction. Any of the extraction techniques disclosed in Perry et al, *Chemical Engineers Hand-book*, $5^{th}$ Edition (McGraw-Hill, 1973) and Lo et al, *Handbook of Solvent Extraction*, Reprint Edition (Krieger, 1991) may be used in the extraction of the third step of our novel process. The process, including the extraction step, may be carried out in a batch mode or continuous or semi-continuous mode of operation.

Countercurrent extraction equipment useful in the present invention include columns, both agitated and non-agitated, mixer-settlers, or centrifugal extractors. Examples of agitated columns include the Karr reciprocating plate, rotating disc, asymmetric disc, Kubni, York-Schiebel, and the Oldshue-Ruihton. Examples of non-agitated columns include spray plate, baffle plate, packed plate, and perforated plast. Examples of centrifugal extractors include those produced by Robatel, Inc., Pittsfield, Mass.; Westphalia Separators, Northvale, N.J. and Baker Perkins, Inc., Saginaw, Mich. The extraction step may be carried by feeding in a countercurrent manner the condensed vapor effluent from step (2) and extraction solvent semi-continuously or continuously to an extractor wherein the condensed vapor effluent from step (2) and extraction solvent are intimately contacted. When the condensed vapor effluent from step (2) is contacted with the extraction solvent, a two-phase mixture is obtained comprising a first phase and a second phase. The first phase comprises a majority of the extraction solvent and the material extracted (or dissolved) from the condensed vapor effluent from step (2). The second phase comprises a majority of the condensed vapor effluent from step (2) and a minor amount of dissolved extraction solvent. In accordance with the present invention, the density of the first phase is less than that of the second phase, permitting separation of the two phases according to means well known in the art. For example, after the condensed vapor effluent from step (2) and the extraction solvent are intimately contacted, the resulting mixture is allowed to separate into two phases. Alternatively, the extraction solvent may be fed to the bottom or lower section, and the condensed vapor effluent from step (2) fed to the top or upper section, of a continuous extraction apparatus wherein the two feeds are intimately mixed. The first phase then is overflowed or removed from the upper section of the apparatus while the second phase exits the lower or bottom.

The extraction of step (3) is carried out at a temperature that provides a two-phase liquid extraction mixture. Thus, the extraction may be carried out at a temperature above the melting point of the condensed vapor effluent from step (2) and less than the boiling point of the extraction solvent. A typical temperature range is about 20° C. up to the boiling point of the extraction mixture. A temperature of about 55° C. has been found to give good results when methanol is used as the extractant. Generally, higher temperatures promote phase separation by inhibiting formation of emulsions of the extractant phase and the phase comprising the majority of the condensed vapor effluent from step (4). Upon completion of the extraction, e.g., the agitation, the mixture is allowed to separate into two phases or layers wherein the upper layer contains most of the extractant, mixed tocols and minor amount of other components of condensed vapor effluent from step (2). The lower layer comprising mixed tocols, squalene, phytosterols and wax is separated from the upper layer. Pressure is not an important process condition and, although the extraction typically is carried out at ambient pressure, pressures moderately above or below ambient pressure may be used.

Step (5) of the recovery process is carried out by cooling the first extraction phase to cause formation of a solid material which is separated from the first phase and combined with the second extraction phase. Generally, step (5) involves cooling, according to conventional means, the first extraction phase to at least 50° C., preferably to at least 20° C. Typically, the first extraction phase is cooled to a temperature in the range of about −40 to about 20° C. Step (5) may be carried out in a batch, semi-continuous or continuous mode of operation.

Step (6) of the process involves combining the second phase collected in step (4) with the precipitate collected in step (5) and removing the extractant employed in step (3) from the materials collected in steps (4) and (5). The extractant may be removed by heating the mixture of materials collected in steps (4) and (5) at a temperature and pressure that vaporizes the extractant. The extractant typically is removed by vaporization at a temperature of about 50 to about 100° C. and a pressure of about 200 to about 1 torr, preferably at a temperature of about 60 to about 80° C. and a pressure of about 100 to about 5 torr. The extent of extractant removal may depend on factors such as the particular extractant employed and the intended use of the lipid composition produced from the process. Normally, the lipid composition product will contain less than about 0.1 weight percent of the extractant. When the extractant is methanol, the lipid composition product will contain less than about 100 ppm methanol, preferably less than about 50 ppm methanol and most preferably less than about 30 ppm methanol, depending on the intended use of the phytolipid composition.

Step (6) of the process may be modified by removing extractant from the second phase collected in step (4) and the precipitate collected in step (5) prior to combining the materials collected in steps (4) and (5). As noted above, the phytolipid composition obtained in accordance with our novel process is substantially free of the extractant(s) used in step (3). The composition is substantially free, i.e., contains less than about 0.1 weight percent, preferably less than about 100 ppm, of water and other solvents such as those used in step (3) or employed as extractants in the process disclosed in U.S. Pat. No. 6,224,717.

The phytolipid composition obtained from the process of the present invention comprises about 10 to about 40 weight percent squalene, about 2 to about 20 weight percent phytosterols, about 1 to about 10 weight percent of mixed tocols, about 40 to about 80 weight percent vegetable wax, and less than 0.1 weight percent solvent. The lipid composition preferably comprises about 15 to about 35 weight percent squalene, about 3 to about 15 weight percent phytosterols, about 2 to about 8 weight percent of mixed tocols, about 45 to about 75 weight percent vegetable wax and less than 0.1 weight percent solvent such as an alkanol and/or acetone extractant. The particular constituents of the lipid compositions depend on the particular vegetable oil by-product employed in the recovery process.

Since the present composition is a complex mixture of many phyto-ingredients, the measured value of the composition also is dependent on the analytical method used, especially with respect to determining the phytosterol content of the composition. Two methods that are useful for phytosterol characterization in complex mixtures are gas chromatography (GC) and carbon 13 NMR (nmr). The GC technique evaluates the presence of a phytosterol component peak by comparing its position and size in the chromatograph with that of a known standard. The phytosterols content of the composition is the sum of the component phytosterol peaks present in the chromatogram. Difficulties can arise from the use of this technique. It is possible that a sterol component is present in the composition and that a standard for that component is not available. This can result in the misidentification or non-identification of a particular component sterol peak, e.g., for a dehydrated sterol. Dehydrated sterols are known to be present in the composition, but are considered to be vegetable wax components.

Such a limitation can be overcome in part by the use of the nmr technique. The nmr more precisely measures the carbon 13 resonance for the sterol. The location of the useful resonances for sterols are distinct and separate from the resonances of dehydrated sterols. However, if a particular phytosterol is present in a low concentration, it is possible that it would be below the detection limit of the nmr instrument, and therefore would not be included in the phytosterol composition. It is therefore useful to use both GC and nmr to quantify the phytosterols present in the composition. Other analytical techniques and combinations of techniques also can be used to determine the phytosterols composition, but each would be subject to its inherent limitations. Mixed tocols (tocopherols and tocotrienols) are generally analyzed by liquid chromatography while GC is the preferred technique for squalene analysis.

The phytolipid compositions obtained from the process of the present invention are further characterized by the following properties: an iodine number of about 50 to about 130 (g iodine per 100 g of lipid composition); a saponification number of about 15 to about 35 mg KOH per g lipid composition; a melting range of about 30 to about 55° C.; an acid number of less than about 2 mg KOH per g lipid composition; and a peroxide value of less than about 10 milliequivalents per kg lipid composition. The low peroxide value of the phytolipid compositions is an indication of the stability of the compositions to oxidation and thus the potential to avoid, or at least limit, the formation of rancid and malodorous compounds.

Phytosterols present in the compositions provided in accordance with the present invention constitute a portion of the unsaponifiable fraction of vegetable oil. More than 40 different phytsosterols have been identified of which β-stigmasterol, stigmasterol and campesterol are the most common. Other phytosterols include sitosterol, cycloartenol, and brassicasterol. The mixed tocols (Vitamin E) consist of eight naturally occurring isomers, four tocopherols (alpha, beta, gamma and delta) and four tocotrienols (alpha, beta, gamma and delta) homologs. The vegetable wax is composed of C24 to C40 hydrocarbons including polycosanes and dehydrated sterols, fatty alcohols (also known as policosanols), and alkyl wax esters. The phytolipid compositions are unique in that they are devoid, or essentially devoid, of tri- and di-glycerides and contain low levels of monoglycerides and free fatty acids. Thus, the total mono-, di- and tri-glycerides and free fatty acids make up less than about 2 weight percent, preferably less than about 1 weight percent of the phytolipid compositions.

The present invention includes a phytolipid composition consisting essentially of about 10 to about 40 weight percent squalene, about 2 to about 20 weight percent phytosterols, about 1 to about 10 weight percent of mixed tocols and about 40 to about 80 weight percent vegetable wax and contains less than about 0.1 weight percent solvent, e.g., alkanol, acetone and/or other extractant. The novel phytolipid composition preferably is derived from rice bran oil and consists essentially of about 15 to about 35 weight percent squalene, about 3 to about 15 weight percent phytosterols, about 2 to about 8 weight percent of mixed tocols, about 45 to about 75 weight percent vegetable wax and less than about 0.1 weight percent solvent.

The phytolipid compositions obtained as described herein have a variety of uses. One such use is a skin care preparation intended for application to human skin comprising the lipid composition as the primary component. Such a skin care composition functions as a skin protectant and moisturizer, e.g., by providing a moisture barrier, and thus serve as a treatment for irritated and dry skin and provide relief of skin irritation, e.g., skin burns, and dry skin. The utility and benefits of the various components of the lipid composition, individually and in combinations, for treating the skin are discussed in the art cited above. The lipid composition provides a mixture of lipid components that provides many outstanding benefits to the skin and lips, and to the skin or lip care product itself. The list of benefits includes: moisturizing, similarity to natural sebum, skin protection with controlled oxygen permeability, natural emolliency, treatment of irritated and dry skin, relief of skin irritation and itching, and anti-inflammatory effects. The benefits of vitamin E or tocopherols are often cited, including inhibition of oxidation of unsaturated lipids, anti-inflammatory properties, soothing effects, and wound healing. See, for example, the discussion in U.S. Pat. No. 5,667,791.

The skin preparation also may contain other ingredients commonly present in products intended for application to human skin. Examples of such other optional ingredients include fragrances, emulsifiers, surfactants, polymeric film formers, film modifiers such as plasticizers, skin conditioning agents (in addition to those provided by the composition of this invention), viscosity increasing or decreasing agents, sunscreen agents, skin-lightening agents, colorants, preservatives, and vitamins (in addition to Vitamin E provided by the composition of this invention). The skin care preparation provides soft, smooth and supple skin. Another use of the lipid composition is as a lip balm to provide relief from chapped lips. The lipid composition may constitute the base of the lip balm along with other conventional lip balm ingredients such as menthol, fragrance, wax, flavoring agents, mineral oil, petrolatum, glycerin, silicones, emulsifiers, other lip conditioning agents, polymeric film formers, film modifiers such as plasticizers, transfer resistance agents, colorants, preservatives, and vitamins. Alternatively, the lip balm may comprise the lipid composition and from about 10 to about 60 weight percent of another wax such as paraffin and/or candelilla wax or from about 10 to about 80 weight percent petrolatum, based on the total weight of the lip balm.

Another advantage inherent in the phytolipid composition provided by the present invention is the ease with which it can be incorporated into cosmetic formulations, particularly emulsions. Thus, the lipid composition also may be used in the formulation of skin and body creams comprised of an emulsion of the lipid and water. Such emulsions may comprise the phytolipid composition and water in phytolipid composition:water weight ratios of about 1:50 to about 2:1. The skin care emulsions also comprise one or more emulsifying agents. The difficulty of solubilizing or dispersing phytosterols is cited in U.S. Pat. Nos. 4,218,334 and 6,087,353. The combination of phytosterols with squalene and rice bran wax (derived from rice bran oil) is particularly easy to formulate with. Upon heating to 55° C., the rice bran wax component melts and, in combination with the squalene, solubilizes the phytosterols. Thus, the phytosterols can be incorporated into a formulation without having to heat them to their melting point of 135 to 140° C. Stable emulsions of the lipid composition may be formulated according to known procedures. For example, to make an oil-in-water emulsion, the lipophilic components are combined and added to the combined hydrophilic components while agitating. Conversely, to make a water-in-oil emulsion, the hydrophilic components are combined and added to the combined lipophilic components while agitating. For both types of emulsions, one or more emulsifiers is used and added to the components in which they are the most soluble. The emulsifiers are selected based on their ability to form stable emulsions given the required HLB (hydrophilic/lipophilic balance) of the formulation components. If any component of the formulation requires melting, both phases should be heated to the required temperature before adding one to the other. Alternatively, oil-in-water emulsions can be prepared using a phase inversion technique. For example, the hydrophilic components are combined and added slowly to the combined lipophilic components while agitating. Given the proper selection of emulsifier, the emulsion will spontaneously change from a water-in-oil to oil-in-water emulsion as indicated by a decrease in viscosity. The phytolipid composition emulsions intended for application to the human skin may contain various ingredients commonly present in such preparation. Examples of such optional ingredients include fragrances, emulsifiers, surfactants, polymeric film formers, film modifiers such as plasticizers, skin conditioning agents (in addition to those provided by the composition of this invention), viscosity increasing or decreasing agents, sunscreen agents, skin-lightening agents, colorants, preservatives, and vitamins (in addition to Vitamin E provided by the composition of this invention).

Because the phytolipid compostion described herein contains the unique composition of naturally occurring antioxidants such as tocopherols, tocotrienols, and squalene, it is auto-stablilized and does not require the incorporation of other antioxidants or hydrogenation to confer chemical stability. Because of this auto-stabilization, the composition is uniquely suited for use as a partial or complete substitute for shortening used in the preparation of food intended for human consumption. For example, the lipid composition may be incorporated into a variety of food products such as:

(1) dairy products such as cheeses, butter, milk and other dairy beverages, spreads and dairy mixes, ice cream and yogurt;

(2) fat-based products such as margarines, spreads, mayonnaise, shortenings, and dressings;

(3) cereal-based products, i.e., food products comprising grains such as bread and pastas;

(4) confectioneries such as chocolate, candies, chewing gum, desserts, non-dairy toppings, sorbets, icings and other fillings;

(5) beverages, both alcoholic and non-alcoholic, such as colas and other soft drinks, juices, dietary supplement and meal replacement drinks; and (6) miscellaneous products such as eggs, processed foods such as soups, pre-prepared pasta sauces, pre-formed meals and the like.

The phytolipid compositions may be incorporated into table spreads such as margarine, low-calorie or light spreads, mustard and mayonnaise in varying concentrations, e.g., from about 0.05 to about 50 weight percent based on the total weight of the fat or oil content of the spread. The phytolipid compositions also may be incorporated into products such as milk fat and vegetable oils intended for human consumption, e.g., in concentrations of about 0.05 to about 50 weight percent based on the total weight of the product. Another food product use of the phytolipid compositions is in beverages including, but not limited to, fat-containing beverages such as citrus-based soft drinks, soy-based milk products, milk-based beverages, smoothies, and nutritionally enhanced and vitamin enriched healthy waters and alcohol-containing, i.e., ethanol-containing, beverages such as citrus-based premixes, wine coolers, malt-based beverages, and malternatives, e.g., alcohol-containing, citrus-flavored beverages having an alcohol content of about 5 weight percent or less, and wine coolers. The concentration of the phytolipid composition in such beverages may be in the range of about 10 to about 1000 parts per million based on the total weight of the beverage.

As mentioned above, the phytolipid compositions may be incorporated into dietary supplements and therapeutic preparations for oral consumption, e.g., by humans, to provide a combination of phytosterols and tocols that have been found to provide the benefits discussed herein above. Such supplements and preparations may be in the form of unit dosages comprising an oil and the phytolipid composition. The phytolipid composition may be dissolved or dispersed in mineral oil or an edible oil such as soybean oil, canola oil, fish oil and the like. The concentration of phytolipid composition present in the base oil may be from about 1 to about 10,000 ppm by weight. An example of a unit dosage form is a capsule, e.g., a soft gelatin capsule, containing an oil having dissolved or dispersed therein from about 1 to about 10,000 ppm by weight of the phytolipid composition.

EXAMPLES

The following example further illustrates the process of the present invention for the recovery of a phytolipid composition. All percentages given are by weight unless otherwise specified.

Example 1

A 3.8 cm (1.5 inches) diameter vacuum-jacketed glass distillation column was equipped with a vacuum pump, refluxing distillation head, reflux ratio controller, metered feed pump, heated feed line, heated feed tank, and collection vessels for the distillate and bottoms product. The column was composed of a rectification section containing 22.9 cm (9 inches) of structured packing below the feed point and a stripping section containing 35.6 cm (14 inches) (both containing structured packing). A reboiler section comprised a 10.2 cm (4 inch) inside diameter, wiped film evaporator with an 45.7 cm (18 inches) length zone that was heated with a hot oil bath and auxiliarily heated with glass jacketed heating sleeve. The non-heated zones were insulated to prevent excessive heat loss. Rice bran fatty acid distillate (RBFAD) containing approximately 30% fatty acid and other low boiling components was fed continuously to the column at a rate of 500 ml/hour while the reboiler temperature was maintained at 298° C. The reflux ratio was 0.5, while the pressure at the top of the column varied between 0.25 and 0.9 torr. After feeding approximately 2.0 liters RBFAD to the feed point, 545 grams of first distillate was collected along with 1247 grams of residue with an acid content of less than 0.2%.

The distillation residue (density 0.87 g/ml) obtained was fed continuously at a rate of approximately 250 muhr to a single-staged, 5.1-cm (2-inch) wiped film still equipped with a heating mantle, feed pump, high vacuum pump, an oil diffusion pump, and distillate and residue receivers. The still was maintained at a pressure of 0.001 to 0.005 torr and a temperature of 230° C. After 1 hour, 59.2 grams of distillate (condensed vapor effluent) and 161.6 grams of second residue were collected. After an additional 1.5 hours, 150 grams of condensed vapor effluent was collected.

The condensed vapor effluent obtained from the second distillation (150 grams) was combined with 1350 grams methanol in a 2-liter, oil-jacketed separatory funnel. The mixture was heated to 55° C. through the use of an external circulating heating/cooling bath, and was stirred with an overhead paddle stirrer. After 15 minutes, agitation was stopped and the mixture was allowed to settle at 55° C. for 20 minutes. 76.6 grams of bottom oil layer was decanted. Residual methanol was removed by heating under vacuum (85° C., 25 torr), yielding 61.9 grams of product as yellow oil. The agitator was turned on and the top methanol layer remaining in the separatory funnel was cooled to −5° C. Upon cooling, a yellow solid precipitate formed. 33.2 grams of yellow methanol-wet precipitate was collected on a chilled (approximately −5° C.) perforated disc vacuum filter (Buchner) funnel. After the methanol was removed (85° C., 25 torr), an additional 24.6 grams of product was isolated.

The combined bottom oil layer and the isolated precipitate comprised 101.2 grams of final product with the following composition:

| | |
|---|---|
| Squalene | 27.9% |
| Phytosterols | 3.0% |
| Vitamin E | 5.8% |
| Rice Bran Wax | Remainder |

Example 2

This example describes the continuous operation of the recovery process with reference to accompanying FIG. 1.

Distillation Step (1)

The vegetable oil by-product, rice bran oil distillate, is fed continuously at a rate of 45.5 kg per hour to distillation step (1). The distillation unit for step (1) comprises two falling film evaporators of 0.38 and 0.8 square meters heated surface, and a thin-film evaporator with a 0.3 square meter heated surface. The distillation unit is operated at a temperature of 240 to 290° C. and a pressure of about 0.2 to 20 torr. The vapor product in step (1) is condensed and removed from the process. The first liquid product is pumped from distillation step (1) at a rate of 32.7 kg per hour to distillation step (2).

Distillation Step (2)

The distillation unit of Step (2) is a short-path evaporator with a 0.8 square meter heated surface. Distillation step (2) is operated at a temperature of 240 to 260° C. and a pressure of 0.0005 to 0.05 torr to produce a second vapor product at a rate of 8.2 kg per hour. The carboxylic acid content of the second vapor product is 1.7% and the tocol content is 146 mg/g. The second liquid product from step (2) is removed from the process.

Extraction Step (3) and 2$^{nd}$ Phase Condensed Vapor Effluent Step (4)

Condensed second vapor product from the second step and methanol are pumped to a mixing tank heated at a temperature of 55° C. in extraction step (3) at rates of 8.2 kg per hour and 57.3 kg per hour, respectively. The vapor product/methanol admixture are pumped to a settling tank with a cone-bottom and where the admixture settles into two phases. The upper first phase extract is removed as a top decant at a rate of 60.9 kg per hour to precipitate collection step (5). The lower second phase is collected in step (4) as a bottom phase decant at a rate of 4.5 kg per hour and is pumped to extractant removal step (6).

Precipitate Collection Step (5)

The first phase extract was maintained at 0° C. through the use of an external heat exchanger to cause formation of a precipitate. The first phase extract is pumped continuously to a centrifuge whereby the precipitate is collected at a rate of 11.4 kg (about 25 pounds) per hour and is pumped to extractant removal step (6).

Extractant Removal Step (6)

The combined intermediate products from step (4) and step (5) (900 kg) are pumped to the column base heater of a distillation column operated at 60-90° C. and 50 to 200 torr. A nitrogen sparge of 150 to 350 standard liters (about 6-12 standard cubic feet) per minute is used to aid in removing the methanol extractant. Over a period of approximately 48 hours, 90.9 kg of methanol extractant is removed. The extractant removed in step (6) is reused in step (3). After removal of the methanol extractant, 818.2 kg of phytolipid product containing less than 50 ppm methanol is obtained.

The following examples further illustrate the utility of the phytolipid composition produced in Example 1.

Example 3

A phytochemical composition produced in accordance with the procedure of Example 1 was determined to have the following composition:

| | |
|---|---|
| Squalene | 27.3% |
| Sterols | 10% |
| Tocopherols | 4.2 wt % |
| Tocotrienols | 1.9 wt % |
| Rice Bran Wax | Remainder of total composition |

This composition was applied directly to the skin and lips. The composition has a very smooth feel on the skin and provides a moisturizing effect to skin and lips.

Examples 4 and 5

The phytolipid composition described in Example 3 was incorporated into skin creams at concentrations of 10% and 20%. Compositions of the skin creams is given below; the components used are by weight percent.

| | Materials Used | |
|---|---|---|
| | Example 4 | Example 5 |
| PART 1 | | |
| Water | 78.3 | 71.3 |
| Glycerin | 2.0 | 2.0 |
| PEG-75 Lanolin | 0.5 | 0.5 |
| Carbomer (Ultrez 10, Noveon) | 0.2 | 0.2 |
| PART 2 | | |
| Cetearyl alcohol (and) Ceteareth-20 (Promulgen D, Amerchol) | 2.0 | 2.0 |
| Glyceryl Dilaurate | 0.5 | 0.5 |
| Cetyl Alcohol | 1.5 | 1.5 |
| Stearic Acid | 1.0 | 1.0 |
| Dimethicone (DC 200 Fluid, Dow Corning) | 0.2 | 0.2 |
| PART 3 | | |
| Sodium Hydroxide, 50% in water | 0.25 | 0.25 |
| PART 4 | | |
| Coco-Caprylate/Caprate (Cetiol LC, Cognis Corp) | 3.0 | 0 |
| Rice Bran Phytolipid Composition | 10.0 | 20.0 |
| PART 5 | | |
| Germaben II (Sutton Laboratories) | 0.5 | 0.5 |

The Part 1 ingredients were combined and heated to 75° C. The Part 2 ingredients were combined and heated to 80° C. Part 2 was added quickly to Part 1 while stirring. Part 3 was added to the mixture of Parts 1 and 2 at 70° C. while stirring. The Part 4 ingredients were combined and heated to 50° C. Part 4 was added to the mixture of Parts 1, 2, & 3 at 50° C. while blending. Part 5 was added with continued blending and cooling. The compositions of Examples 3 and 4 produced light yellow creams. Both creams provide a very smooth feel on the skin that has a less greasy feeling than the composition of Example 2 alone.

Example 6

A lip balm was prepared from 8.0 g of the phytolipid composition described in Example 3 and 2.0 g candelilla wax. The two components were melted, and then combined by stirring. After cooling to room temperature, the mixture had a consistency that is typical of a lip balm product. The composition has a very smooth feel on the lips, which remains until the product is removed or rubbed off.

Example 7

A lip balm was prepared from 6.0 g of the phytolipid composition described in Example 3 and 4.0 g parafin wax. The two components were melted, and then combined by stirring. After cooling to room temperature, the mixture had a consistency that is typical of a lip balm product. The composition has a very smooth feel on the lips, which remains until the product is removed or rubbed off.

Example 8

A lip balm was prepared from 7.0 g of the phytolipid composition described in Example 3 and 3.0 g of white petrolatum. The two materials were melted and then combined by stirring. After cooling to room temperature, the mixture had a consistency that is typical of a lip balm product. The composition has a very smooth feel on the lips.

Example 9

Preparation of a Nutritious Beverage

To 55 g of orange oil are added 88 g of sucrose acetate isobutyrate previously heated to approximately 60° C. and 55 g of the phytolipid composition described in Example 3 previously melted at approximately 50° C. The temperature of the resulting mixture is maintained in the range of 40-50° C. A portion (180 g) of this oil solution is emulsified by addition under vigorous agitation to an aqueous phase consisting of 667 g water, 2 g citric acid, 1 g sodium benzoate, and 150 g modified food starch. The resulting emulsion is de-aerated overnight and then homogenized using an APB Gaulin lab homogenizer, Model 15MR-8TA, operated at 6000 psi (two passes) to prepare a stable beverage emulsion. A beverage syrup is prepared by combining 3 g of the above beverage emulsion with 197 g of 55% aqueous sucrose solution. The final beverage is prepared by combining 80 g of the above beverage syrup with 400 g of carbonated water. The beverage is bottled and sealed for storage. This beverage contains approximately 60 mg of rice bran lipid.

Example 10

Preparation of a Nutritious Food Spread

Locust bean gum (2.5 g) and corn oil (175 g) are combined in an agitated vessel until a homogeneous mixture is obtained. To this are then added 30 g sodium caseinate and 40 g of skim milk powder, followed by addition of 225 g of skim milk and 30 g of buttermilk. The mixture is then homogenized at 2,500 psi, and to the resulting homogenate is added 2.5 g of lactic acid. The resulting semi-solid is pasteurized at 170° F. for 30 minutes. During pasteurization, melted composition (15 g) of Example 2 is added directly and the resulting product is homogenized again at 2,500 psi. Following homogenization, the product is packaged and stored.

Example 11

Preparation of a Nutritious Mayonnaise

In a planetary mixer are combined 50 g of fluid egg yolk, 15 g of salt, 20 g of sugar, 5 g of mustard flour and 1 g of flavorings and spices. The mixture is stirred until homogeneous and cooled to about 15° C. The phytolipid composition described in Example 2 (50 g) and soybean oil (700 g) are combined, agitated, and warmed to about 50° C. to homogeneously disperse the rice bran lipid product. This oil mixture and vinegar (40 g) are added simultaneously as two streams to the contents of the mixer and stirring is continued at about 15° C. until the batch of mayonnaise becomes homogeneous. The resulting product is removed and stored in plastic container.

Example 12

Preparation of Nutritious Peanut Butter Cookies

Sucrose (120 g), brown sugar (120 g), peanut butter (100 g), nonfat dry milk (5 g), whole egg solids (15 g), salt 5 g), vanilla (2 g), cake flour (200 g) and baking soda (4 g) are combined in a mixing bowl. In a separate container, shortening (100 g) is melted and 15 g of the phytolipid composition described in Example 2 is added. The liquefied shortening mixture is then added directly to the dry mixture prepared above. The total mix is then stirred until homogeneous, transferred to cake pan, and baked for 10 minutes at 425° F.

The invention has been described in detail with particular reference to preferred embodiments thereof, but it will be understood that variations and modifications can be effected within the spirit and scope of the invention.

We claim:

1. A process for preparing a phytolipid composition comprising squalene, phytosterols, tocopherols and vegetable wax which comprises the steps of:
   (1) distilling a vegetable oil by-product comprised of mixed tocols, fatty acids, hydrocarbons, vegetable waxes, sterol esters of fatty acids, sterols, triterpenoid alcohols, squalene, methyl-sterols, and mono-, di-, and triglycerides at a temperature of about 170 to about 320° C. and a pressure of about 0.1 to about 35 torr to produce (i) a vapor product comprising fatty acids and low boiling hydrocarbons and (ii) a liquid product;
   (2) distilling the liquid product of step (1) at a temperature of about 230 to about 300° C. and a pressure of about 0.0005 to about 1 torr to produce (i) a second vapor product comprising a mixed tocols concentrate, squalene, phytosterols, and vegetable wax and (ii) a second liquid product;
   (3): condensing the vapor product and mixing the condensed vapor product with an extractant of an alkanol or a mixture of acetone and water to form a mixture, separating the mixture into two phases comprising (i) a first phase comprising a majority of the extractant and (ii) a second phase comprising a majority of the condensed vapor product;
   (4) collecting the second phase formed in step (3);
   (5) cooling the first phase formed in step (3) to effect formation of a precipitate followed by collection of the precipitate; and
   (6) combining the second phase collected in step (4) with the precipitate collected in step (5) and removing extractant employed in step (3) from the materials collected in steps (4) and (5),
whereby a phytolipid composition comprising about 10 to about 40 weight percent squalene, about 2 to about 20 weight percent phytosterols, about 1 to about 10 weight percent of mixed tocols and about 40 to about 80 weight percent vegetable wax is obtained.

2. The process according to claim 1 wherein the vegetable oil by-product is derived from palm oil or rice bran oil and the phytolipid composition obtained comprises about 15 to about 35 weight percent squalene, about 3 to about 15 weight percent phytosterols, about 2 to about 8 weight percent of mixed tocols, about 45 to about 75 weight percent vegetable wax and less than about 0.1 weight percent extractant/solvent.

3. A process for preparing a phytolipid composition comprising squalene, phytosterols, tocopherols and vegetable wax which comprises the steps of:
   (1) distilling a vegetable oil by-product comprised of mixed tocols, fatty acids, hydrocarbons, vegetable waxes, sterol esters of fatty acids, sterols, triterpenoid alcohols, squalene, methyl-sterols, and mono-, di-, and triglycerides at a temperature of about 170 to about 320° C. and a pressure of about 0.1 to about 35 torr to produce (i) a vapor product comprising fatty acids and low boiling hydrocarbons and (ii) a liquid product;
   (2) distilling the liquid product of step (1) at a temperature of about 230 to about 300° C. and a pressure of about 0.0005 to about 1 torr to produce (i) a second vapor product comprising a mixed tocols concentrate, squalene, phytosterols, and vegetable wax and (ii) a second liquid product;
   (3) condensing the vapor product and mixing the condensed vapor product with an extractant of an alkanol or a mixture of acetone and water to form a mixture, separating the mixture into two phases comprising (i) a first phase comprising a majority of the extractant and (ii) a second phase comprising a majority of the condensed vapor product;

(4) collecting the second phase formed in step (3) and removing the extractant employed in step (3);

(5) cooling the first phase formed in step (3) to effect formation of a precipitate followed by collection of the precipitate and removal the of the extractant employed in step (3); and (6) combining the second phase collected in step (4) with the precipitate collected in step (5), whereby a phytochemical composition comprising about 10 to about 40 weight percent squalene, about 2 to about 20 weight percent phytosterols, about 1 to about 10 weight percent of mixed tocols and about 40 to about 80 weight percent vegetable wax is obtained.

4. The process according to claim 3 wherein the vegetable oil by-product is derived from palm oil or rice bran oil and the phytochemical composition obtained comprises about 15 to about 35 weight percent squalene, about 3 to about 15 weight percent phytosterols, about 2 to about 8 weight percent of mixed tocols, about 45 to about 75 weight percent vegetable wax and less than about 0.1 weight percent extractant/solvent.

5. A process for preparing a phytochemical composition comprising squalene, phytosterols, tocopherols and vegetable wax which comprises the steps of:

(1) distilling a rice bran oil by-product comprised of mixed tocols, fatty acids, hydrocarbons, vegetable waxes, sterol esters of fatty acids, sterols, triterpenoid alcohols, squalene, methyl-sterols, and mono-, di-, and triglycerides at a temperature of about 240 to about 290° C. and a pressure of about 0.2 to about 20 torr to produce (i) a vapor product comprising fatty acids and low boiling hydrocarbons and (ii) a liquid product;

(2) distilling the liquid product of step (1) at a temperature of about 230 to about 260° C. and a pressure of about 0.005 to about 0.5 torr to produce (i) a second vapor product comprising a mixed tocols concentrate, squalene, phytosterols, and vegetable wax and (ii) a second liquid product;

(3) condensing the vapor product and mixing the condensed vapor product with an extractant selected from the group consisting of methanol, ethanol, propanol, and 2-propanol wherein the volume:volume ratio of extractant:condensed vapor product is about 6:1 to 12:1 separating the mixture into two phases comprising (i) a first phase comprising a majority of the extractant and (ii) a second phase comprising a majority of the condensed vapor product;

(4) collecting the second phase formed in step (3);

(5) cooling the first phase formed in step (3) to effect formation of a precipitate followed by collection of the precipitate; and (6) combining the second phase collected in step (4) with the precipitate collected in step (5) and heating the materials collected in steps (4) and (5) at a temperature of about 50 to about 100° C. and a pressure of about 200 to about 1 Torr to remove extractant employed in step (3), whereby a phytolipid composition comprising about 15 to about 35 weight percent squalene, about 3 to about 15 weight percent phytosterols, about 2 to about 8 weight percent of mixed tocols, about 45 to about 75 weight percent vegetable wax and less than about 0.1 weight percent extractant/solvent is obtained.

6. The process according to claim 5 wherein the extractant employed in step (3) is methanol and the phytolipid composition obtained contains less than about 100 ppm methanol.

\* \* \* \* \*